United States Patent [19]

Umemura et al.

[11] 4,260,810
[45] Apr. 7, 1981

[54] PROCESS FOR PREPARING DIESTERS OF DICARBOXYLIC ACIDS

[75] Inventors: Sumio Umemura; Kanenobu Matsui; Yoshinari Ikeda; Katsuro Masunaga; Takumi Kadota; Kozo Fujii; Keigo Nishihira; Masaoki Matsuda, all of Ube, Japan

[73] Assignee: Ube Industries, Ltd., Ube, Japan

[21] Appl. No.: 52,341

[22] Filed: Jun. 27, 1979

[30] Foreign Application Priority Data

Jul. 3, 1978 [JP] Japan .................................. 53/79801

[51] Int. Cl.³ ...................... C07C 67/38; C07C 69/34; C07C 69/75; C07C 69/612
[52] U.S. Cl. .................................... 560/204; 560/80; 560/81; 560/121; 560/127; 560/193
[58] Field of Search ................... 560/204, 80, 81, 121, 560/127, 193

[56] References Cited

U.S. PATENT DOCUMENTS 4,138,580   2/1979   Umemura et al. .................... 560/204

FOREIGN PATENT DOCUMENTS 1142750   2/1969   United Kingdom ..................... 560/204

*Primary Examiner*—Joseph E. Evans
*Attorney, Agent, or Firm*—Frishauf, Holtz, Goodman & Woodward

[57] ABSTRACT

A process for preparing a diester of a dicarboxylic acid having two more carbon atoms than the unsaturated hydrocarbon used as a starting material, which comprises subjecting an unsaturated hydrocarbon, carbon monoxide and an ester of nitrous acid to catalytic vapor phase reaction at a temperature of 50° to 200° C. in the presence of a platinum group metal or a salt thereof and a halogen compound.

16 Claims, No Drawings

PROCESS FOR PREPARING DIESTERS OF DICARBOXYLIC ACIDS

This invention relates to a novel process for preparing a diester of a dicarboxylic acid by way of a vapor phase reaction. More particularly, this invention relates to a process for preparing a diester of a dicarboxylic acid corresponding to the unsaturated hydrocarbon used as a starting material, namely a diester of a dicarboxylic acid having two more carbon atoms than the unsaturated hydrocarbon used, which comprises subjecting an unsaturated hydrocarbon, carbon monoxide and an ester of nitrous acid to catalytic vapor phase reaction in the presence of a platinum group metal or a salt thereof and a halogen compound with optional introduction of molecular oxygen into the reaction system.

According to this invention, a diester of succinic acid is obtained when ethylene is used as the unsaturated hydrocarbon, and diesters of dicarboxylic acids such as substituted succinic acid, substituted or unsubstituted maleic acid and cycloalkane dicarboxylic acid are obtained as the diester of dicarboxylic acid when an unsaturated hydrocarbon other than ethylene is used as the starting material. For example, when propylene is used as the unsaturated hydrocarbon, diesters of methylsuccinic acid and of glutaric acid are obtained; when cyclohexene is used, a mixture of diesters of 1,2-and 1,3-cyclohexane dicarboxylic acids is obtained; and when acetylene is used, a diester of maleic acid is obtained.

So far has widely been known a process for preparing a diester of a dicarboxylic acid having two more carbon atoms than the unsaturated hydrocarbon used as the starting material, which comprises subjecting an unsaturated hydrocarbon, carbon monoxide and an alcohol to reaction, introducing molecular oxygen into the reaction system as occasion demands, and various catalysts have been proposed for the reaction.

All of the conventionally proposed processes are based on liquid phase reaction under pressure. According to the conventional processes, by-products are produced in larger amounts; the selectivity to the desired product is low; and thus the recovery of the product, catalyst, etc., from the reaction mixture has been troublesome.

As a result of extensive studies by the present inventors to develop an industrial process for preparing a diester of dicarboxylic acid by way of a vapor phase catalytic reaction which has never been proposed, it was found that a diester of a dicarboxylic acid having two more carbon atoms than the unsaturated hydrocarbon used as a starting material can be produced industrially by subjecting an unsaturated hydrocarbon, carbon monoxide and an ester of nitrous acid to vapor phase catalytic reaction in the presence of a platinum group metal or a salt thereof and a halogen compound at a temperature of 50° to 200° C. and accomplished this invention.

According to this invention, a diester of a dicarboxylic acid can be produced by a vapor phase reaction of an unsaturated hydrocarbon, carbon monoxide and an ester of nitrous acid, which have never been proposed; various problems in the conventional liquid phase reaction, of an unsaturated hydrocarbon, carbon monoxide and an alcohol have been solved; and thus a diester of a dicarboxylic acid can advantageously be produced industrially.

Namely, the process according to this invention has many advantageous points as follows:

(i) Even under ordinary or reduced pressure under which a diester of a dicarboxylic acid is not substantially produced according to the liquid phase reaction as proposed conventionally, a diester of a dicarboxylic acid can be produced in high selectivity with high space time yield. Accordingly, an expensive apparatus for high-pressure reaction is not required and power for compressing the starting materials can be reduced.

(ii) As the catalyst is solid and is used on a fixed bed or a fluidized bed, it is not necessary to set a special apparatus for separating the reaction product from the catalyst. Further, as the reaction is a vapor phase one, loss of the catalyst due to the dissolution thereof in a reaction medium, which is observed frequently in the conventional liquid phase reaction, does not occur in this invention.

(iii) The endurance of the catalyst is high and so the catalyst can be used for a long period of time.

The present invention will be explained further in detail as follows.

As the unsaturated hydrocarbons used in this invention are aliphatic and alicyclic hydrocarbons having 2 to 20 carbon atoms such as ethylene, propylene, butene, pentene, hexene, heptene, octene, nonene, decene, undecene, dodecene, tridecene, tetradecene, pentadecene, hexadecene, heptadecene, octadecene, nonadecene, eicosene and their isomers, and cyclopentene, cyclohexene, cycloheptene, cyclooctene, indene, styrene, allene, methylallene, butadiene, pentadiene, hexadiene, cyclopentadiene, etc.; and acetylene or its alkyl derivatives.

These unsaturated hydrocarbons may be used as such or may be used in a diluted form with an inert gas such as nitrogen gas. The concentration of the unsaturated hydrocarbon to be supplied to the reaction region may be varied over a wide range, a range of 5 to 80% by volume based on the starting material gas being selected ordinarily.

The preferable ester of nitrous acid used in the process of this invention is an ester of nitrous acid with a saturated monohydric aliphatic alcohol having 1 to 8 carbon atoms or an alicyclic alcohol having 1 to 8 carbon atoms. As the alcohol component may be mentioned an aliphatic alcohol such as methanol, ethanol, n-propanol, isopropanol, n-butanol, isobutanol, sec-butanol, tert-butanol, n-amyl alcohol, isoamly alcohol, hexanol, octanol, etc., and an alicyclic alcohol such as cyclohexanol, methylcyclohexanol, etc. These alcohol may contain therein a substituent such as an alkoxy group which does not inhibit the reaction.

While the amount of the ester of nitrous acid to be used may be changed over a wide range, it is necessary to make exist the ester of nitrous acid in the reaction system so that its concentration in the gaseous material which is introduced into the reactor may be not less than 0.5% by volume.

The higher the concentration of an ester of nitrous acid is, the more speedily the reaction proceeds. However, the upper limit may necessarily be selected so that a liquid phase of products may not be accumulated in the reaction zone. The ester of nitrous acid is used usually in an amount of 1 to 20% by volume.

Carbon monoxide to be used in the process of this invention may be pure or may be diluted with an inert gas such as nitrogen etc. The concentration of carbon monoxide in the reaction zone may vary over a wide range and usually is in the range of 5 to 80% by volume.

The catalyst to be used in the process according to this invention is a platinum group metal such as palladium, platinum, rhodium, ruthenium, iridium and osmium, or a salt thereof such as halide, nitrate, sulfate, phosphate, acetate, oxalate and benzoate, which may preferably be used in the form of supported catalyst on such carriers as activated carbon, alumina, silica, diatomaceous earth, pumice, zeolite, molecular sieve, etc. The amount of the catalyst to be supported on a carrier is 0.01 to 10%, preferably 0.5 to 2% by weight based on the carrier.

The halogen compound used in this invention is effective in accelerating the desired reaction and inhibiting the side-reactions, and thus enhances the yield and selectivity of the desired product. Namely, when the reaction is carried out in the absence of a halogen compound, the reaction between carbon monoxide and an ester of nitrous acid is prominent to form larger amount of a diester of oxalic acid. In contrast to that, in the presence of one or more halogen compounds in the reaction system, the side-reaction is inhibited and the reaction of an unsaturated hydrocarbon, carbon monoxide and an ester of nitrous acid is accelerated to produce the desired compound, i.e., a diester of a dicarboxylic acid corresponding to the unsaturated hydrocarbon, in high yield and selectivity.

As such a halogen compound, any compound containing a halogen atom such as chlorine, bromine and iodine is effective and there may be mentioned, for example, a halide of a platinum group metal, a halide of an alkali metal or an alkaline earth metal such as sodium, potassium, magnesium, calcium, ets.; a halide of a metal (or a transition metal) such as iron group metals (cobalt, nickel, iron), copper, zinc, chromium, antimony, tin, manganese, etc.; an ammonium halide; and so on.

Of the metal halide compounds mentioned above, a metal halide selected from halides of alkali metals, alkaline earth metals, iron group metals, platinum group metals, copper, zinc, chromium, antimony, tin and manganese.

These halides may be supported, together with the above-mentioned catalyst, on a carrier.

A non-metallic vaporizable halogen compound such as halogenide, methyl chloroformate, phosgene, nitrosyl halide may be introduced in a gaseous form into the reaction zone.

When a platinum group metal halide is used, other halogen compound may not necessarily be combined therewith since the platinum group metal halide is also a halogen compound.

The halogen compound may be used in an amount of 0.01 to 100 gram atoms, preferably 0.05 to 50 gram atoms, calculated on the halogen atom, per 1 gram atom of the platinum group metal used as the catalyst, in cases where the halogen compound is a metal halide and is used as a supported form on a carrier together with the catalyst. In cases where it is a vaporizable non-metallic compound and is used by introduction thereof into the reaction zone in a gaseous state, the amount thereof may be not less than 10 ppm, preferably 100 ppm of the gaseous mixture supplied to the reactor.

The preparation of the supported catalyst to be used in the process according to this invention may be carried out by any conventional method in which a catalyst component is supported on a carrier. For instance, a platinum group metal or a salt thereof and a halogen compound are dissolved in an aqueous hydrochloric acid and the resulting solution is impregnated in or applied to a carrier, followed by drying to give a supported catalyst.

In the process of this invention, when relatively high concentration of an ester of nitrous acid is used, the reaction proceeds in sufficiently high speed even at a considerably low temperature, and the lower the reaction temperature is, the less side-products are formed. In such a case, however, the reaction is inhibited when a liquid phase is formed in the reaction zone. Accordingly, it is advantageous to carry out the reaction at relatively low temperature while maintaining the desired space time yield. The reaction temperature, preferably is in the range of 50° to 200° C. preferably 70° to 150° C. The reaction pressure may be in a range where a liquid phase is not accumulated in the reaction zone. While ordinary pressure may usually be sufficient, the reaction system may be under slightly higher pressure or under slightly reduced pressure depending upon the starting material.

The process of this invention is practiced by using a reactor of fixed bed or fluidized bed. The contact time during which a gaseous material contacts with a solid catalyst is not more than 10 seconds, preferably 0.2 to 5 seconds.

In this invention, molecular oxygen may be introduced into the reaction system to increase further the yield and the selectivity of the desired product. The molecular oxygen means oxygen gas, air and other oxygen-containing gas obtained by dilution of oxygen with such an inert gas as nitrogen.

Next, the present invention will further be explained in more detail by way of the Examples and Comparative examples shown below. In each of the Examples and Comparative examples, the experiment was run by using a tubular reactor made of glass, which had an inner diameter of 25 mm. and was 500 mm. in length. For analysis, the condensate which was collected by cooling an outlet gas with a condenser was subjected to gaschromatography.

EXAMPLE 1

In an aqueous hydrochloric acid containing 0.21 g. of palladium chloride, there was immersed an activated carbon, and the mixture was evaporated to dryness and then dried further at 120° C. to give a catalyst supported on an activated carbon (1 wt. % Pd).

After 20 ml. of the thus obtained catalyst was placed in the tubular reactor and the temperature was maintained at 120° C., there was supplied a gaseous mixture consisting of 17 vol. % of ethyl nitrite, 57 vol. % of ethylene, 14 vol. % of carbon monoxide and 12 vol. % of nitrogen at a rate of 600 ml./min. As the result, it was found that the space time yield of diethyl succinate was 45 g/l.Cat.hr.

EXAMPLES 2-7

In an aqueous hydrochloric acid containing 0.21 g. of palladium chloride and a predetermined amount of each of various halogen compounds (shown in Table 1), there was immersed 12 g. of an activated carbon, and the mixture was evaporated to dryness and then dried further at 120° C. to give a catalyst supported on an activated carbon (1 wt. % Pd). By using the thus obtained catalyst, the reaction was carried out in the same manner as in Example 1.

The experimental results of Examples 2 to 7 are shown in Table 1.

TABLE 1

| Exam. No. | Halogen compound for preparation of catalyst | | Cl/Pd (atomic ratio) of prepared catalyst | Diethyl succinate formed* (space time yield, g/l. Cat. hr) |
| --- | --- | --- | --- | --- |
| | Compound | Used Amount (g) | | |
| 2 | CuCl$_2$ | 0.25 | 5.1 | 120–150 |
| 3 | CuCl$_2$ | 1.0 | 28.3 | 290 |
| | KCl | 1.2 | | |
| 4 | CuCl$_2$ | 1.0 | 17.5 | 80–110 |
| | NaCl | 0.2 | | |
| 5 | CuCl$_2$ | 1.0 | 38.6 | 330 |
| | LiCl | 1.2 | | |
| 6 | FeCl$_2$ | 0.25 | 5.3 | 50 |
| 7 | BaCl$_2$ | 0.25 | 4.0 | 55 |

*Note:
By-products such as diethyl oxalate were hardly detected.

EXAMPLE 8

A palladium-on-silica gel bead (2 wt. % Pd) was immersed in an aqueous solution of cupric chloride containing copper atoms in an amount of ten times the palladium atoms, the mixture was allowed to stand overnight and evaporated to dryness to give a catalyst supported on the silica bead [Cl/Pd (atomic ratio)=22.0].

After 17 ml. of the thus obtained catalyst was placed in the tubular reactor and the temperature inside the catalyst layer was maintained at 145° C., a gaseous mixture consisting of 20 vol. % of ethylene, 22 vol. % of carbon monoxide, 5 vol. % of methyl nitrite, 30 vol. % of oxygen and 22 vol. % of nitrogen was supplied at a rate of 700 ml./min., and 36 wt. %-hydrochloric acid further was supplied simultaneously, after evaporated in a carburettor, at a rate of 0.5–2 ml./hr.

EXAMPLE 9

In an aqueous hydrochloric acid containing 0.2 g. of palladium chloride and 0.5 g. of cupric chloride was immersed 12 g. of an activated carbon, and the mixture was evaporated to dryness and then dried further at 120° C. to give a catalyst supported on an activated carbon [1 wt. % Pd, Cl/Pd (atomic ratio)=8.6].

After 20 ml. of the thus obtained catalyst was placed in the tubular reactor and the temperature inside the catalyst layer was maintained at 120° C., a gaseous mixture consisting of 1.5 vol. % of ethyl nitrite, 28 vol. % of ethylene, 41 vol. % of carbon monoxide and 29.5 vol. % of nitrogen was supplied at a rate of 850 ml./min.

As the result, it was found that the space time yield of diethyl succinate was 80 to 100 g./l.·Cat.·hr. and that of by-produced diethyl carbonate was 4 to 6 g./l.·Cat.·Hr.

EXAMPLE 10

After 10 ml. of a catalyst prepared in the same manner as in Example 9 was placed in the tubular reactor and the temperature inside the catalyst layer was maintained, a gaseous mixture consisting of 3 vol. % of methyl nitrite, 28 vol. % of isobutylene, 30 vol. % of carbon monoxide and 39 vol. % of nitrogen was supplied at a rate of 830 ml./min. As the result, it was found that the space time yield of dimethyl 3-methylglutarate was 140 g/l.·Cat.·hr.

EXAMPLE 11

An experiment was run in the same manner as in Example 10 except that the isobutylene was replaced with 28 vol. % of propylene and the resulting gaseous mixture was supplied at a rate of 900 ml./min. As the result, it was found that the space time yields of dimethyl methylsuccinate and dimethyl glutarate were 73 g./l.·Cat.·Hr. and 103 g./l.·Cat.·hr., respectively, and extremely small amount of dimethyl oxalate was by-produced.

EXAMPLE 12

After 10 ml. of a catalyst prepared in the same manner as in Example 9 was placed in the tubular reactor and the temperature inside the catalyst layer was maintained at 110° C. Subsequently, a gaseous mixture consisting of 2.7 vol. % of methyl nitrite, 31 vol. % of carbon monoxide and 66.3 vol. % of nitrogen was supplied, after bubbled through a mixture of α-olefins having 6, 8 or 10 carbon atoms, into the above-mentioned tubular reactor at a rate of 1000 ml./min.

As the result, a mixture of dimethyl 1,2-dicarboxylates was obtained in a space time yield of 60 g./l.·Cat.·hr.

EXAMPLE 13

After 20 g. of palladium-on-alumina (1 wt. % Pd) was immersed in an aqueous hydrobromic acid solution containing 4.2 g. of cupric bromide, the mixture was evaporated to dryness and then dried further at 120° C. to give a catalyst supported on an alumina [Br/Pd (atomic ratio)=20.0].

Then, after 20 ml. of the thus prepared catalyst was placed in the tubular reactor and the temperature inside the catalyst layer was maintained at 110° C., a gaseous mixture consisting of 4 vol. % of methyl nitrite, 30 vol. % of ethylene, 30 vol. % of carbon monoxide, 3 vol. % of oxygen and 33 vol. % of nitrogen was supplied at a rate of 800 ml./min.

As the result, it was found that the space time yield of dimethyl succinate was 50 g./l.·Cat.·hr.

EXAMPLE 14

After 20 ml. of a palladium-on-alumina (1 wt. % Pd) was immersed in an aqueous hydrochloric acid solution containing 3.2 g. of cupric chloride dihydrate, the mixture was evaporated to dryness and then dried further at 120° C. to give a catalyst supported on an alumina [Cl/Pd (atomic ratio)=20.0].

Then, after 20 ml. of the thus obtained catalyst was placed in the tubular reactor and the temperature inside the catalyst layer was maintained at 110° C., a gaseous mixture consisting of 5 vol. % of methyl nitrite, 30 vol. % of ethylene, 30 vol. % of carbon monoxide, 4.0 vol. % of oxygen, 2.0 vol. % of methyl chloroformate and 29 vol % of nitrogen was supplied at a rate of 800 ml./min.

As the result, it was found that dimethyl succinate was obtained in a space time yield of 75 g./l.·Cat.·hr.

EXAMPLE 15

In the tubular reactor was packed 20 ml. of palladium-on-alumina catalyst (1 wt. % Pd) and a gaseous mixture having the same composition as in Example 14 and supplied at a rate of 800 ml./min.

As the result, dimethyl succinate was found to be produced in a space time yield of 4.5 g./l.·Cat.·hr.

EXAMPLES 16–21

After 10 ml. of a catalyst prepared in the same manner as in Example 9 was packed in the tubular reactor and the temperature inside the catalyst layer was maintained, a gaseous mixture consisting of 2.7 vol. % of each ester of nitrous acid (shown in Table 2), 30 vol. % of ethylene, 30 vol. % of carbon monoxide and 37.3 vol. % of nitrogen was supplied at a rate of 900 ml./min.

The results are shown in Table 2.

TABLE 2

| Example No. | Ester of nitrous acid | Product* (Space time yield, g./l. Cat. . hr.) |
|---|---|---|
| 16 | n-butyl nitrite | di-n-butyl succinate (71) |
| 17 | n-amyl nitrite | di-n-amyl succinate (34) |
| 18 | isoamyl nitrite | diisoamyl succinate (36) |
| 19 | sec-butyl nitrite | di-sec-butyl succinate (30) |
| 20 | isobutyl nitrite | diisobutyl succinate (96) |
| 21 | n-propyl nitrite | di-n-propyl succinate (163) |

*By-products such as a diester of oxalic acid were hardly detected.

COMPARATIVE EXAMPLE 1

16 ml. of palladium-on-activated carbon catalyst (2 weight% Pd) was placed in the reactor. After raising the temperature of the catalyst layer at 130° C., a gaseous mixture containing 13 vol.% of ethylene, 16 vol.% of carbon monoxide, 4 vol.% of oxygen, 3% vol.% of methyl nitrite and 64 vol.% of nitrogen was supplied to the reactor at a rate of 1000 ml./min.

As the result, the space time yield of the desired product, dimethyl succinate, was only 7 gram/l.·Cat.·hr. while that of undesired product, dimethyl oxalate, was 62 g./l.·Cat.·hr.

COMPARATIVE EXAMPLE 2

The same experiment as Comparative example 1, except that a palladium nitrate-on-activated carbon catalyst (1 weight% Pd) was used instead of the catalyst specified above.

As the result, the space time yield of the desired product, dimethyl succinate, was only 3 g./l.·Cat.·hr. while that of the undesired product, dimethyl oxalate, was 73 g./l.·Cat.·hr.

We claim:

1. A process for preparing a diester of a dicarboxylic acid having two more carbon atoms than the unsaturated hydrocarbon used as a starting material, which comprises subjecting an unsaturated hydrocarbon, carbon monoxide and an ester of nitrous acid to catalytic vapor phase reaction at a temperature of 50° to 200° C. in the presence of a platinum group metal or a salt thereof and a halogen compound;
    said unsaturated hydrocarbon being at least one aliphatic or alicyclic hydrocarbon containing one or two double bonds and containing 2 to 20 carbon atoms; and
    said halogen compound is a metal halide selected from halides of alkali metals, alkaline earth metals, iron group metals, platinum group metals, copper, zinc, chromium, antimony, tin and manganese, or a vaporizable, non-metallic halogen compound selected from hydrogen halogenide, methyl chloroformate, phosgene and nitrosyl halide.

2. A process as claimed in claim 1, in which said reaction is carried out in the presence of molecular oxygen.

3. A process as claimed in claim 1, in which said ester of nitrous acid is an ester of nitrous acid with a saturated aliphatic monohydric alcohol having 1 to 8 carbon atoms or an alicyclic alcohol.

4. A process as claimed in claim 1, in which platinum group metal or a salt thereof is supported on a carrier.

5. A process as claimed in claim 1, in which said platinum group metal is palladium.

6. A process as claimed in claim 1, in which said unsaturated hydrocarbon is at least one selected from the group consisting of ethylene, propylene, butene, pentene, hexene, heptene, octene, nonene, decene, undecene, dodecene, tridecene, tetradecene, pentadecene, hexadecene, heptadecene, octadecene, nonadecene, eicosene and their isomers, cyclopentene, cyclohexene, cycloheptene, cyclooctene, indene, styrene, allene, methylallene, butadiene, pentadiene, hexadiene, and cyclopentadiene.

7. A process as claimed in claim 1, in which said unsaturated hydrocarbon is ethylene, propylene or butene.

8. A process as claimed in claim 1, in which said unsaturated hydrocarbon is used in an amount of 5 to 80% by volume.

9. A process as claimed in claim 1, in which said carbon monoxide is used in an amount of 5 to 80% by volume.

10. A process as claimed in claim 1, in which said ester of nitrous acid is used in an amount of 1 to 20% by volume.

11. A process as claimed in claim 1, in which said reaction is carried out at a temperature of 70° to 150° C.

12. A process as claimed in claim 1 wherein said unsaturated hydrocarbon is ethylene.

13. A process as claimed in claim 1 or 2 which said halogen compound is a metal halide selected from halides of copper, iron, sodium, potassium, lithium and barium, or a vaporizable non-metallic compound selected from hydrogen chloride and methyl chloroformate.

14. A process as claimed in claim 1, 12 or 13 in which said halogen compound is used in a amount of 0.01 to 100 gram atoms, calculated on the halogen atom, per 1 gram atom of the platinum group metal, in cases where said halogen compound is a metal halide, and in an amount of not less than 10 ppm, calculated on the compound per se, of the gaseous mixture in cases where said halogen compound is a vaporizable non-metallic compound.

15. A process for preparing a diester of a dicarboxylic acid having two more carbon atoms than the unsaturated hydrocarbon used as a starting material, which comprises subjecting an unsaturated hydrocarbon, carbon monoxide and an ester of nitrous acid to catalytic vapor phase reaction at a temperature of 50° to 200° C. in the presence of a platinum group metal or a salt thereof and a halogen compound;
    said halogen compound is used in an amount of 0.01 to 100 gram atoms, calculated on the halogen atom, per 1 gram atom of the platinum group metal, in cases where said halogen compound is a metal halide, and in an amount of not less than 10 ppm, calculated on the compound per se, of the gaseous mixture in cases where said halogen compound is a vaporizable non-metallic compound; and
    wherein said ester of nitrous acid is an ester of nitrous acid with a saturated aliphatic monohydric alcohol having 1 to 8 carbon atoms or an alicyclic alcohol;

wherein said platinum group metal is palladium supported on a carrier; wherein said unsaturated hydrocarbon is ethylene, propylene or butene; and wherein said unsaturated hydrocarbon is in an amount of 5 to 80% by volume; said carbon monoxide is in an amount of 5 to 80% by volume, and said ester of nitrous acid is in an amount of 1 to 20% by volume.

16. A process as claimed in claim 15 wherein said reaction is carried out in the presence of molecular oxygen.

* * * * *